United States Patent [19]
Kamerling

[11] Patent Number: 5,217,459
[45] Date of Patent: Jun. 8, 1993

[54] METHOD AND INSTRUMENT FOR PERFORMING EYE SURGERY

[76] Inventor: William Kamerling, 423 Clements Bridge Rd., Barrington, N.J. 08007

[21] Appl. No.: 750,825

[22] Filed: Aug. 27, 1991

[51] Int. Cl.⁵ .............................................. A61B 17/38
[52] U.S. Cl. ........................................ 606/48; 606/4; 606/32; 606/45; 606/51; 606/52
[58] Field of Search ........................ 606/6, 107, 4, 166, 606/48, 50, 51, 52, 43, 210, 45, 46, 167, 49; 604/22

[56] References Cited

U.S. PATENT DOCUMENTS

| | | | |
|---|---|---|---|
| 3,945,375 | 3/1976 | Banko | 128/6 |
| 4,567,890 | 2/1986 | Ohta et al. | 606/51 |
| 4,985,030 | 1/1991 | Melzer et al. | 606/51 |
| 5,026,370 | 6/1991 | Lottick | 606/42 |

Primary Examiner—Stephen C. Pellegrino
Assistant Examiner—S. C. Harris
Attorney, Agent, or Firm—Stuart E. Beck

[57] ABSTRACT

An instrument for surgically removing a lens from the eye comprising a housing that supports electrodes for bipolar cutting and splitting the nucleus of the lens.

A method of surgically removing a lens from the eye comprising the steps of inserting an instrument into the eye, cutting a groove in the nucleus of the lens with electrical energy, splitting the nucleus at the groove, and removing the pieces of nucleus from the eye.

10 Claims, 1 Drawing Sheet

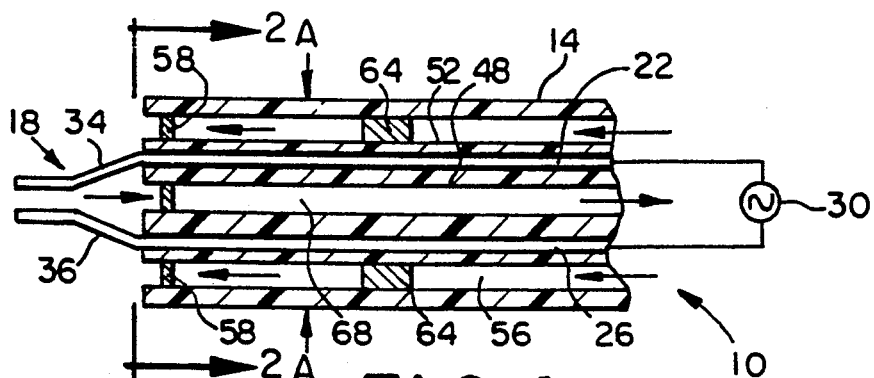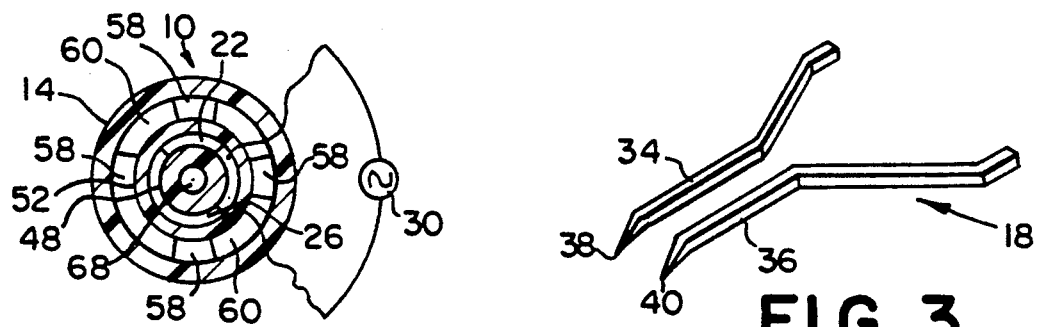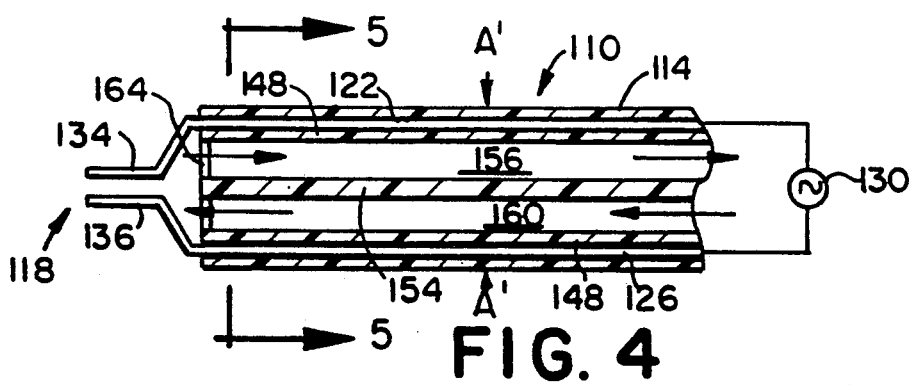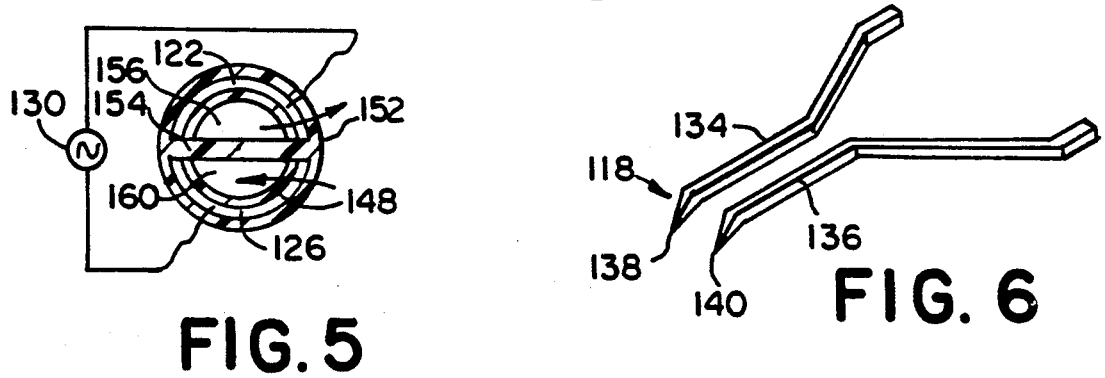

METHOD AND INSTRUMENT FOR PERFORMING EYE SURGERY

BACKGROUND OF THE INVENTION

Field of the Invention

This invention relates to an instrument for performing eye surgery, and more particularly to a method and instrument which takes advantage of bipolar cutting to remove the lens from the eye through a small incision while reducing the number of times that the instrument has to be passed through the incision.

From time to time the lens of the eye becomes opacified to the extent that vision is impossible. Opacified lenses are termed cataracts.

There is no presently known technology or treatment which will reverse the opacification of the lens. Accordingly, the preferred method of treatment for cataracts has been to surgically remove the lens and then to compensate for that removal by the substitution of an artificial lens.

The lens comprises a capsule which includes anterior and posterior portions. The capsule contains a nucleus surrounded by a cortex. The nucleus is comprised of relatively hard material while the cortex is a jelly-like material. There are currently several surgical methods for removing the lens. A common method is phacoemulsification. This procedure requires an incision into a portion of the eye called the limbus. A capsulotomy is then performed. This comprises an incision in the anterior capsule. A suitable ultrasound generating instrument of a type well known in the art is inserted through the incision into the capsule. The ultrasound emulsifies the nucleus into small pieces. The pieces of nucleus are then withdrawn from the eye and an artificial lens is substituted.

Many eye surgeons are uneasy about using this procedure since there is risk that the ultrasound will tear the posterior capsule and that fragments of the nucleus of the lens will be lost in the vitreous of the eye.

It is also known to remove the lens by phacofragmentation. In this procedure the surgeon inserts an anvil behind the nucleus and then cuts through the nucleus against the anvil with a knife. The cut sections of the nucleus are then withdrawn through the incision. The anvil is used because cutting completely through the nucleus entails the risk that the posterior capsule will be cut and the nuclear fragments will go into the vitreous of the eye from which they are difficult to remove.

It would be advantageous to have an instrument which would avoid the problems associated with phacoemulsification and be able to cut the anterior capsule and remove the nucleus without the need for a second instrument and without the need for the instruments to be inserted and removed from the eye several times during the surgery.

With the foregoing in mind the invention relates generally to an instrument for surgically removing the lens from the eye comprising means for cutting a groove in the lens and splitting the lens at the groove, and means for removing the pieces of lens.

In another aspect, the invention relates to a method for removing the lens from the eye comprising the steps of removing the anterior capsule, cutting a groove in the nucleus of the lens with a bipolar cutter, separating the lens into at least two pieces and removing the pieces.

BRIEF DESCRIPTION OF THE DRAWING

The invention will be better understood and further advantages and uses thereof will be readily apparent when considered in view of the following detailed description of exemplary embodiments, taken with the accompanying drawing in which:

FIG. 1 is a side view partially in section of one presently preferred embodiment of the invention.

FIG. 2 is a section view taken along line 2—2 of FIG. 1.

FIG. 3 is an enlarged perspective view of a portion of the device shown in FIG. 1.

FIG. 4 is a side view partially in section of another preferred embodiment of the invention.

FIG. 5 is a section view taken along lines 5—5 of FIG. 4.

FIG. 6 is an enlarged perspective view of a portion of the device shown in FIG. 4.

Referring to FIG. 1, an instrument 10 constructed in accordance with one presently preferred embodiment of the invention is illustrated. The instrument comprises a housing 14 which serves as a support and hand grip for the instrument. The housing may be made from a suitable stiff, yet flexible material. Supported within the housing are means for bipolar cutting.

Bipolar cutting is a way for cutting tissue by application of a relatively high frequency, low voltage sine wave cutting current. It is believed that the tissue is cut by molecular resonance in response to the current generated by the bipolar cutter.

Bipolar cutting is relatively well known. A device for providing a suitable voltage for accomplishing bipolar cutting is the Malis Bipolar Coagulator, model CMC-1, which is made by Valley Forge Scientific, Inc. of Valley Forge, Pa.

The bipolar cutter 18 comprises first and second elongated relatively stiff electrodes 22 and 26 which are disposed within housing 14. They are connected by suitable means to a source of voltage illustrated schematically at 30. The distal ends 34 and 36 of the electrodes 22 and 26 are in spaced parallel relation to each other. They extend from within the housing 14 a distance great enough to enable them to extend through the incision cut in the eye to thereby engage the anterior capsule and then the nucleus of the lens to cut them.

For bipolar cutting to occur the distal ends 34 and 36 of the first and second electrodes must be spaced from each other. Further, it is preferred that the distal ends 34 and 36 come to points 38 and 40 since it is at the points that the cutting current will be realized. If the distal ends are blunted, cutting will not be effective. On the other hand, if the procedure is such that only one of the ends can be observed during cutting, then that end should be pointed while the other end should be blunted since the cutting will take place adjacent the pointed tip rather than the one that is blunt.

An annular member of stiff, flexible non-conductive material 48 is disposed within the housing to support the inner portions of the electrodes 22 and 26. A second annular member 52 made of non-conductive material in coaxial relation to member 48 is disposed adjacent the first and second electrodes 22 and 26. Thus, the electrodes are retained in spaced circumferential relation by being disposed between non-conductive annular members 48 and 52.

The annular space between member 52 and housing 14 comprises a conduit 56 through which an irrigating solution, preferably comprising saline, can be conducted to the surface of the tissue adjacent the distal ends of the electrodes 22 and 26 to assist in increasing the conductivity of the tissue in the area where cutting is to take place while at the same time providing a cooling bath for the surrounding tissue so that likelihood of burning or other damage as a result of the applied current will be minimized.

A first plurality of circumferentially spaced, rigid members 58 that define a plurality of circumferentially spaced passages 60 are disposed between the housing 14 and the annular layer of insulation 52 at the end of the instrument near the bi-polar cutter 18.

A second plurality of circumferentially spaced, rigid members 64 that define a plurality of circumferentially spaced passages (not shown) are disposed between the housing 14 and the annular layer of insulation 52 in the midportion of the instrument.

The annular non-conductive member 48 defines an interior passageway 68 through which the saline solution, debris and other unwanted materials can be removed with the assistance of a suitable vacuum aspirator.

Referring now to FIGS. 4 and 5 a second preferred embodiment of an instrument 110 comprising the invention is illustrated. It includes an annular housing 114 made from a suitable stiff yet flexible material which comprises a support and grip for the instrument. The bipolar cutter 118 comprises first and second elongated, stiff, flexible electrodes 122 and 126 which are connected to a suitable source of electric power 130.

The distal ends 134 and 136 of electrodes 122 and 126 are disposed in spaced parallel relation to each other and are long enough to extend through the incision as explained earlier. As described above, it is preferred that each distal end come to a sharp point 138, 140 to enable better control of the cutting.

As seen in FIG. 5, the electrodes 122 and 126 are contained within an inner layer 148 of non-conductive material and an outer layer 152 of non-conductive material. The layers 148 and 152 are coaxial and are supported on a diametrically extending, elongated member 154 made of non-conductive material.

As can be seen in FIGS. 4 and 5 the relationship of the respective electrodes 122 and 126, and the non-conductive layers 148, 152 within which they are contained and the non-conductive element 154 define first and second conduits 156 and 160. Preferably, one of the conduits such as conduit 156 can be employed advantageously to conduct an irrigating fluid such as the saline solution mentioned above into the region where cutting is to take place. The other conduit 160 can be used to aspirate the debris associated with the surgery.

A rigid annulus 164 may be imbedded in or attached in a suitable manner to the end of housing 114 near the bipolar cutter 118.

The surgical procedure in which the instrument comprising the invention is used comprises the making of an incision along the limbus to allow entry into the anterior chamber. Typically, the incision is no more than 3 mm. in length. The instrument is then inserted through the incision and the electrodes 22, 26 and 122, 126 are energized to provide a cutting current which can then be used to remove the anterior capsule. Simultaneous with the cutting, the tissue in the area where the cutting is taking place is bathed in a saline solution which is delivered through the irrigating conduits in the respective embodiments of the instrument. The provision of the saline irrigation enhances the cutting capabilities of the instrument while at the same time cools the surrounding tissue.

The cutting can be used to further reduce the size of the segments of the anterior capsule so that they may be withdrawn through the aspirating conduit 68 and 160.

After the anterior capsule is removed the distal end 40 and 140 of the electrodes can be inserted through the cortex and passed over the nucleus of the lens while energized. This will cause a groove to be cut in the nucleus. The width of the groove will be slightly greater than the distance between the distal ends of the electrodes. More than one pass of the distal end of the electrode may be necessary to cut a groove of sufficient depth. Preferably, a groove of about two thirds of the thickness of the nucleus is desired in order to enable easy splitting of the nucleus.

After a groove of adequate depth is cut in the nucleus, the electrodes can be de-energized and the instrument moved so that the electrodes lie within the groove.

When the surgeon squeezes the housing 14, 114 as shown by the arrows A and A', the distal ends of the of the electrodes swing outwardly around circumferential members 58 and annulus 164 away from each other. Since the electrodes are relatively stiff and the groove in the nucleus is deep, the nucleus will be split in two pieces by the electrodes.

If the pieces of the nucleus are large, the aspirator can be used to move them into the anterior chamber where they can be washed out of the eye with the irrigating fluid or fluid from any convenient source. On the other hand, if the pieces of the nucleus are small, they can be removed from the eye by being aspirated through the aspirating conduit.

After the nuclear debris and cortex has been evacuated from the eye, an artificial lens can be installed in its place.

What has been described is a method and instrument for cataract surgery. The method and apparatus avoid the problems of prior methods and instruments by constructing the instrument so that the cutting electrodes also split the nucleus. These features have the advantage of providing the surgeon with precise control over the cutting of the anterior capsule and the nucleus.

Further, this offers the advantage of a relatively fast procedure without the requirements for repeated insertion and removal of the instrument from the eye.

While the invention has been described with respect to certain embodiments, it is apparent that other embodiments will be obvious to those skilled in the art in view of the foregoing description. Thus, the scope of the invention should not be limited by the description, but, rather, only by the scope of the claims appended hereto.

I claim:

1. An instrument for surgical removal of the lens from the eye comprising
    a support, said support including an elongated, hollow housing that has a stiff, flexible annular wall,
    means for cutting a groove in the nucleus of the lens with bipolar electrical energy and splitting the nucleus at the groove, said last named means comprising energizable first and second electrodes that are carried by said support, said electrodes including distal ends that are operative when energized to generate a tissue cutting electrical energy, and
    a conduit for removing the pieces of nucleus, means for connecting said conduit to a source of vacuum, said electrodes and said conduit being disposed within said annular wall, and rigid means at the end of said housing adjacent the distal ends of said electrodes, said rigid means co-operating with said stiff, flexible annular wall to cause the distal ends of said electrodes to move away from each other to split the nucleus.

2. An instrument for surgical removal of the lens from the eye comprising first and second coaxial, hollow, elongated, stiff, flexible members made of electrically non-conductive material, said first hollow member being disposed within said second hollow member, means for cutting a groove in the nucleus of the lens with bipolar energy and splitting the nucleus into pieces at the groove, said last named means comprising first and second electrodes, said electrodes including distal ends, said electrodes being disposed in circumferentially spaced relation to each other and being disposed between said first and second hollow members to electrically isolate them, and said first hollow member comprises means for removing the pieces of the lens.

3. An instrument as defined in claim 2 including a third hollow, elongated, stiff, flexible member, said first and second hollow, elongated members being received within said third hollow member and being spaced therefrom, the space between said second hollow member and said third hollow member defining a conduit for the delivery of an irrigating fluid to area where the groove is being cut, and means disposed in the space between said second and third hollow members to transfer a squeezing of said third hollow member to said electrodes to cause the distal ends of said electrodes to swing outwardly away from each other to split the nucleus.

4. An instrument as defined in claim 3 wherein said means disposed in the space between said second and third hollow members comprises a plurality of rigid members that define a plurality of circumferentially spaced passages.

5. An instrument for surgical removal of the lens from the eye comprising means for cutting a groove in the nucleus of the lens with bipolar electrical energy and splitting the nucleus at the groove into pieces, and means for removing the pieces of nucleus, means for cutting a groove in the nucleus of the lens with bipolar electrical energy and splitting the nucleus at the groove comprising first and second electrodes, said electrodes including distal ends, said electrodes being in mutually-facing relation, an elongated diametrically extending, non-conductive member disposed between said electrodes to electrically separate them from each other, and each of said electrodes cooperates with said non-conductive member to define a first conduit for applying an irrigating fluid to the area where cutting is taking place and a second conduit for removing material from said area.

6. An instrument as defined in claim 5 including first and second coaxial layers of concentric electrically non-conductive, stiff, flexible material disposed on each side of said diametrically extending, elongated non-conductive member, and each of said electrodes is disposed between said coaxial layers on each side of said diametrically extending, elongated non-conductive member.

7. An instrument as defined in claim 6 including a rigid annular member supported by said third member at its end adjacent the distal ends of said electrodes.

8. The method of surgically removing the lens from the eye comprising the steps of cutting a groove in the nucleus of the lens with bipolar electrical energy, splitting said nucleus, and removing the pieces of nucleus.

9. The method as defined in claim 8 wherein said steps of cutting, splitting and removing are accomplished by using an instrument that remains in the eye during and between said steps.

10. The method as defined in claim 9 including the step of applying an irrigating fluid to the nucleus during cutting.

* * * * *